United States Patent [19]

Mercado et al.

[11] Patent Number: 5,013,543

[45] Date of Patent: May 7, 1991

[54] COSMETIC EYELINER FORMULATION

[75] Inventors: Clara Mercado, Aberdeen; Amit R. Shah, Iselin, both of N.J.

[73] Assignee: Revlon, Inc., New York, N.Y.

[21] Appl. No.: 270,429

[22] Filed: Nov. 9, 1988

Related U.S. Application Data

[63] Continuation of Ser. No. 873,568, Jun. 12, 1986, abandoned.

[51] Int. Cl.$^5$ .............................................. A61K 7/021
[52] U.S. Cl. ........................................ 424/63; 424/80; 514/844
[58] Field of Search ................... 424/63, 80; 514/844

[56] References Cited

U.S. PATENT DOCUMENTS

| | | | |
|---|---|---|---|
| 3,691,273 | 9/1972 | Marcarian et al. | 424/63 |
| 4,423,031 | 12/1983 | Murui et al. | 424/63 |
| 4,452,989 | 6/1984 | Deckner et al. | 424/63 X |

FOREIGN PATENT DOCUMENTS 1027913  7/1986  Japan ...................................... 424/63

*Primary Examiner*—John W. Rollins

[57] ABSTRACT

A cosmetic eyeliner composition in the form of a liquid is provided which is especially adapted for use in conjunction with a wick-type nib pen which delivers eyeliner through a capillary action, which eyeliner composition includes a pigment intermediate formed of FDA approved inorganic eye product pigments having an average particle size of about 5 microns or less, a water-soluble organic polymer film-former, such as polyvinyl pyrrolidone, and optionally one or more plasticizers, and a carrier for the pigment intermediate, which carrier includes water, plasticizer, preservative, and an alcohol and optionally a moisturizer and/or humectant. The eyeliner composition of the invention will pass through the wick of a wick-type nib pen by capillary action without clogging the wick.

6 Claims, No Drawings

COSMETIC EYELINER FORMULATION

This is a continuation of application Ser. No. 873,568 filed June 12, 1986, now abandoned.

FIELD OF THE INVENTION

The present invention relates to an eyeliner composition which is especially adapted for delivery by a wick-type nib pen and includes FDA approved eye product pigments.

BACKGROUND OF THE INVENTION

A wick-type nib pen which delivers a steady flow of coloring liquid has been available in Europe and Japan as a delivery system for eyeliner cosmetics. The nib pen is similar in construction to cartridge-type pens and includes a shell portion having a wick formed of urethane-nylon of desired porosity extending out from one end, which shell is adapted to hold a liquid eyeliner cartridge in connection with the wick. The liquid eyeliner flows from the cartridge into the wick and is subsequently delivered by capillary action to the user.

Pigments employed in the nib pen liquid eyeliner are water-soluble organic colors and carbon black pigments which are easily solubilized and flow through the wick without clogging same.

Unfortunately, such water-soluble organic colors are not approved for use in eye cosmetics in the U.S. Those pigments approved by the FDA for use in eye products are conventional inorganic pigments, such as iron oxides, which are not readily water-soluble but are water-dispersible. The approved FDA pigments are available only in relatively large particle size which will not allow such pigment particles to pass through the wick of a nib pen without causing undue clogging. Accordingly, a need exists in the U.S. for an eyeliner composition which may be employed with a wick-type nib pen and will contain FDA approved eye product pigments.

BRIEF STATEMENT OF THE INVENTION

In accordance with the present invention, an eyeliner composition is provided which may be delivered by wicking action from a nib pen and which is formed of a pigment intermediate containing pigment particles having an average particle size of 5 microns or less, and a carrier for the pigment intermediate. The pigment intermediate includes one or more FDA approved water-dispersable pigments and a water-soluble polymer film-forming agent, which preferably is polyvinyl pyrrolidone, and optionally one or more plasticizers. The carrier for the pigment intermediate includes water, one or more plasticizers, one or more quick drying alcohols, and one or more preservatives, and optionally one or more moisturizers and/or optionally one or more humectants.

DETAILED DESCRIPTION OF THE INVENTION

The eyeliner composition of the invention will contain pigment intermediate in an amount within the range of from about 30 to about 70% and preferably from about 40 to about 60% by weight of the total eyeliner composition and the carrier will be present in an amount within the range of from about 70 to about 30% and preferably from about 60 to about 40% by weight.

The pigment intermediate employed in the eyeliner composition of the invention will include one or more FDA approved water-dispersible inorganic eye product pigments in an amount within the range of from about 20 to about 70% by weight and preferably from about 40 to about 60% by weight based on the total weight of the pigment intermediate. These pigments will be ground, if necessary, to an average particle size of 5 microns or less and preferably a particle size so that the smallest particles present will be no more than from about 4 to about 5 microns. Examples of such FDA approved pigments include, but are not limited to, iron oxides, to produce colors such as black, iron blue, green, brown, red or yellow.

The water-soluble aqueous polymer film-forming agent will preferably comprise polyvinyl pyrrolidone which is available under the tradenames PVP, Plasdone, Polyclar AT, Peregal SKT, Kollidon and Albigen A. The above film-forming agent (that is, polyvinyl pyrrolidone) will be employed in the pigment intermediate in amounts within the range of from about 25 to about 60% and preferably from about 35 to about 55% by weight of the total pigment intermediate.

In addition, the pigment intermediate will optionally include a plasticizer for the film-forming agent which may include polysorbate 20, propylene glycol, carboxymethyl cellulose, cellulose acetate, cellulose acetate propionate, dibutyl tartrate, diethylene glycol, dimethylene phthalate, glycerine, shellac, sorbitol or oleyl alcohol with polysorbate 20 being preferred. Polysorbate 20 is a mixture of laurate esters of sorbitol or sorbitol anhydrides, formed predominantly of the mono ester and condensed with approximately 20 moles of ethylene oxide. The plasticizer for the pigment intermediate will be employed in an amount within the range of from about 2 to about 15% and preferably from about 5 to about 10% by weight of the pigment intermediate.

The carrier for the pigment intermediate includes water in an amount within the range of from about 25 to about 50% and preferably from about 30 to about 45% by weight based on the total weight of carrier and pigment intermediate.

In addition, the carrier will include one or more plasticizers in an amount within the range of from about 1 to about 7% by weight and preferably from about 2 to about 6% by weight based on the total weight of the carrier and pigment intermediate. Examples of plasticizers suitable for use herein include but are not limited to polysorbate 20, propylene glycol or glycerine, as well as any of the plasticizers which may be employed in the pigment intermediate with propylene glycol, a mixture of propylene glycol and glycerine or a mixture of propylene glycol and polysorbate 20 being preferred.

The carrier will also include a quick drying alcohol, such as ethanol, in an amount within the range of from about 3 to about 10% and preferably from about 5 to about 8% by weight of the total carrier and pigment intermediate.

A preservative may also be present in the carrier, such as phenoxy ethanol, ethyl paraben, butyl paraben, methyl paraben, propyl paraben, imidazolinyl urea, dimethydimethoyl hydantoin, N-(3-chloroallyl) hexaminium chloride, cetrimonium bromide, trisodium ethylene diamine tetraacetic acid and/or butylated hydroxy anisole with a mixture of phenoxy ethanol and one or more parabens being preferred. The preservative will be present in an amount within the range of from about 0.1 to about 2% and preferably from about 0.5 to about 1% by weight of the total carrier and pigment intermediate.

Various other conventional ingredients which may optionally be present in the carrier include one or more moisturizers, such as L-pyroglutamic acid, hydrolyzed animal collagen, hydrolyzed animal protein, with L-pyroglutamic acid being preferred, in an amount within the range of from 0 to about 0.5% and preferably from about 0.02 to about 0.2% by weight of the total carrier and pigment intermediate.

Preferred eyeliner compositions of the invention are set out below.

| Ingredient | Parts by Weight |
|---|---|
| A. Pigment Intermediate | |
| Polyvinyl pyrrolidone | 35 to 55 |
| Pigment (having an average particle size of less than about 5 microns) | 40 to 60 |
| Polysorbate 20 | 0.5 to 1.0 |
| Propylene glycol | 2.0 to 7.0 |
| Complete Eyeliner Formulation | |
| A. Pigment Intermediate | 40 to 60 |
| B. Carrier | |
| purified water | 30 to 45 |
| propylene glycol | 1 to 3 |
| Polysorbate 20 | 0.5 to 1.5 |
| L-pyroglutamic acid | 0 to 0.2 |
| glycerin | 0 to 1 |
| ethanol (quick drying alcohol) | 5 to 10 |
| Preservative (preferably Phenonip*) | 0.5 to 1.0 |

| | Parts by Weight per 100 parts preservative |
|---|---|
| *Phenonip | |
| Phenoxy ethanol | 72 |
| Ethylparaben | 4 |
| Butylparaben | 6 |
| Methylparaben | 16 |
| Propylparaben | 2 |

The above eyeliner composition is especially suited for use with a cartridge type nib pen in that the pigments present therein will have an average particle size of less than about 5 microns and will therefore pass through the wick of the nib pen by capillary action without causing clogging.

In forming the eyeliner of the invention, the pigment intermediate is prepared by mixing the film-former agent (polyvinyl pyrrolidone), pigment and preservative and passing the mixture through a two roller mill to grind the pigment particles down to an average particle size of no more than from about 4 to about 5 microns. The mixture is removed from the roller mill in the form of chips or sheets. The carrier components, namely, the water, optionally moisturizers, preservatives and optionally humectants will be mixed together and heated to a temperature of within the range of from about 70° to about 80° C. The pigment intermediate is then added to the above mixture using a Lighnin mixer or other appropriate agitator, and mixing is continued for about 1 to about 2 hours until all chips or sheets are dissolved. The mixture is cooled to a temperature within the range of from about 28° to about 35° C. and preservative and quick drying alcohol are added. Mixing is continued until a uniform mixture is obtained. The mixture is then filtered through a 5 micron filter pad. The so-formed mix may then be inserted into a cartridge which may be fed into a nib-type pen equipped with a wick.

The following Examples represent preferred embodiments of the present invention.

EXAMPLE 1

An eyeliner composition containing FDA approved pigments that can be applied by a nib pen having the following composition was prepared as described below.

| | | % W/W |
|---|---|---|
| B. Pigment Intermediate | | |
| Polyvinyl pyrrolidone (film-former) | | 44.0 |
| Iron oxide pigments | black 10% blue 40% | 50.0 |
| Polysorbate 20 | (plasticizer) | 1.0 |
| Propylene glycol | | 5.0 |
| | | 100.0 |
| Eyeliner Composition | | |
| A. Purified Water | | 41.0 |
| Propylene glycol | plasticizer | 2.5 |
| Polysorbate 20 | | 1.0 |
| B. Pigment intermediate* | | 50.0 |
| C. Phenonip** (preservative) | | .5 |
| Ethanol (quick drying alcohol) | | 5.0 |
| | | 100.0 |

| | % by Weight of Preservative Present |
|---|---|
| **Phenonip | |
| Phenoxy ethanol | .36 |
| Ethyl paraben | .02 |
| Butyl paraben | .03 |
| Methyl paraben | .08 |
| Propyl paraben | .01 |

Phase B ingredients were ground through a roller mill to achieve an average particle size of 4 to 5 microns or less.

Phase A ingredients were added to a suitable vessel and heated to 75° C. to form a solution. Phases A and B were then mixed in a Lighnin mixer for 1 hour until Phase B was dissolved. The so-formed solution A-B was cooled to 50° C. and Phase C was added and mixing was continued for 15 minutes until a uniform liquid eyeliner composition was obtained which was then passed through a 5 micron filter pad.

The resulting liquid eyeliner composition was found to be suitable for use in a wick-type nib eyeliner pen and was delivered by capillary action without clogging the wick and pen.

EXAMPLE 2

An eyeliner composition containing FDA approved pigments that can be delivered by a nib pen having the following composition was prepared as described below.

| | | % W/W |
|---|---|---|
| B. Pigment Intermediate | | |
| Polyvinyl pyrrolidone (film-former) | | 39.0 |
| Pigment | green 53% black 7% | 60.0 |
| Polysorbate 20 (plasticizer) | | 1.0 |
| | | 100.0 |
| Eyeliner Composition | | |
| A. Purified Water | | 36.2 |
| L-Pyroglutamic acid (moisturizer) | | 0.1 |
| Propylene glycol (plasticizer) | | 2.3 |

| -continued | |
|---|---|
| Glycerine (humectant-plasticizer) | 0.6 |
| B. Pigment intermediate* | 50.0 |
| C. Phenonip (preservative) | 0.8 |
| Ethanol (quick drying alcohol) | 10.0 |
| | 100.0 |

Phase B ingredients were ground through a two roller mill to achieve an average particle size of 4 to 5 microns or less.

Phase A ingredients were added to a suitable vessel and heated to 75° C. to form a solution. Phases A and B were then mixed in a Lighnin mixer for 1 hour until Phase B was dissolved. The so-formed solution A-B was cooled to 50° C. and Phase C was added and mixing was continued for 15 minutes until a uniform liquid eyeliner composition was obtained which was passed through a 5 micron filter pad.

The resulting liquid eyeliner composition was found to be suitable for use in a wick-type nib eyeliner pen and was delivered by capillary action without clogging the wick and pen.

What is claimed is:

1. A cosmetic eyeliner composition in the form of a flowable liquid dispersion or solution suitable for application with a wick-type nib pen consisting of:
   40-60 % of a pigment intermediate substantially free of a fatty oxyethylenated alcohol ether surface active agent,
   30-45% water,
   5-10% ethanol
   1-6% plasticizer selected from the group consisting of propylene glycol and polysorbate 20,
   0.5-1.0% preservative selected from the group consisting of phenoxyethanol and one or more alkyl parabens, wherein said pigment intermediate consists of
   40-60% by weight of said pigment intermediate of a pigment having an average particle size of 5 microns or less selected from the group consisting of FDA approved inorganic eye product pigments, carmine pigments and mixtures thereof,
   35-55% by weight of said pigment intermediate of polyvinylpyrrolidone,
   2-15% by weight of said pigment intermediate of a plasticizer selected from the group consisting of propylene glycol and polysorbate 20.

2. The composition of claim 1 wherein the FDA approved pigment is one or more iron oxides.

3. The composition of claim 1 consisting essentially of about:
   50.0% of pigment intermediate
   41.0% water
   5.0% ethanol
   2.5% propylene glycol
   1.0% polysorbate 20
   0.5% preservative
   wherein said pigment intermediate consists essentially of about:
   50.0% pigments
   44.0% polyvinylpyrrolidone
   1.0% polysorbate 20
   5.0% propylene glycol.

4. A cosmetic eyeliner composition in the form of a flowable liquid dispersion or solution suitable for application with a wick-type nib pen consisting of:
   40-60% of a pigment intermediate substantially free of oxyethylenated alcohol ether surface active agent
   30-45% water
   5-10% ethanol
   1-6% of a plasticizer selected from the group consisting of propylene glycol and glycerin
   0.02-0.2% L-pyroglutamic acid
   0.5-1% of a preservative selected from the group consisting of phenoxyethanol, one ore more alkyl parabens, or mixtures thereof;
   wherein said pigment intermediate consists essentially of:
   40-60% by weight of said pigment intermediate of a pigment having an average particle size of 5 microns or less selected from the group consisting of FDA approved inorganic eye produce pigments, carmine pigments and mixtures thereof,
   33-55% by weight of said pigment intermediate of polyvinyl pyrrolidone, and
   about 1.0% polysorbate 20.

5. The composition of claim 4 wherein the FDA approved pigment is one or more iron oxides.

6. THe composition of claim 4 consisting essentially of about:
   50.0% pigment intermediate
   36.2% water
   10.0% ethanol
   2.3% propylene glycol
   0.6% glycerin
   0.1% L-pyroglutamic acid
   0.8% preservative
   wherein said pigment intermediate consists essentially of about:
   60.0% pigments
   39.0% polyvinylpyrrolidone
   1.0% polysorbate 20.

* * * * *